United States Patent
Gisser et al.

(10) Patent No.: US 10,364,357 B2
(45) Date of Patent: *Jul. 30, 2019

(54) HIGH QUALITY ANTIMICROBIAL PAINT COMPOSITION

(71) Applicant: THE SHERWIN-WILLIAMS COMPANY, Cleveland, OH (US)

(72) Inventors: Kathleen R Gisser, Solon, OH (US); Morgan S Sibbald, Copley, OH (US); Wanda J Smith, Macedonia, OH (US); Janice K. Dreshar, Westlake, OH (US); Donald A. Prochazka, Strongsville, OH (US)

(73) Assignee: THE SHERWIN-WILLIAMS COMPANY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/823,123

(22) Filed: Aug. 11, 2015

(65) Prior Publication Data

US 2016/0007596 A1 Jan. 14, 2016

Related U.S. Application Data

(63) Continuation of application No. 13/552,966, filed on Jul. 19, 2012, now Pat. No. 9,131,683.

(60) Provisional application No. 61/541,168, filed on Sep. 30, 2011.

(51) Int. Cl.
| | |
|---|---|
| *C08K 5/17* | (2006.01) |
| *C09D 5/16* | (2006.01) |
| *C09D 7/40* | (2018.01) |
| *A01N 25/04* | (2006.01) |
| *A01N 25/28* | (2006.01) |
| *A01N 59/16* | (2006.01) |
| *C09D 5/14* | (2006.01) |
| *A01N 33/12* | (2006.01) |

(52) U.S. Cl.
CPC .............. *C09D 5/14* (2013.01); *A01N 25/28* (2013.01); *A01N 33/12* (2013.01); *C08K 5/17* (2013.01); *C09D 5/1625* (2013.01); *C09D 7/69* (2018.01)

(58) Field of Classification Search
CPC ................................. C09D 5/14; A01N 33/12
See application file for complete search history.

(56) References Cited

U.S. PATENT DOCUMENTS

| | | | | | |
|---|---|---|---|---|---|
| 4,018,611 | A | * | 4/1977 | Cramer ................ | D06M 16/00 106/18.32 |
| 5,173,110 | A | * | 12/1992 | Stovicek ................ | A01N 25/24 106/15.05 |
| 5,314,719 | A | * | 5/1994 | Batdorf ................ | C09D 5/14 106/15.05 |
| 6,238,732 | B1 | * | 5/2001 | Cameron ................ | C08J 3/124 264/130 |
| 6,365,066 | B1 | * | 4/2002 | Podszun ................ | C09D 5/1625 106/15.05 |
| 9,131,683 | B2 | * | 9/2015 | Gisser ................ | C09D 5/14 |
| 2004/0219128 | A1 | * | 11/2004 | Batdorf ................ | A01N 25/10 424/78.27 |
| 2005/0249880 | A1 | * | 11/2005 | Wallace ................ | A01N 25/04 427/372.2 |
| 2007/0266901 | A1 | * | 11/2007 | Rance ................ | C08L 3/02 106/501.1 |
| 2015/0029813 | A1 | * | 1/2015 | Berghaus ................ | G01J 3/0205 366/140 |

FOREIGN PATENT DOCUMENTS

| | | | |
|---|---|---|---|
| CN | 101481562 A * | 7/2009 | |
| WO | WO 2011032845 A2 * | 3/2011 | ............. A01N 25/10 |

OTHER PUBLICATIONS

Machine translated English language equivalent of CN 101481562 (Jul. 2009, 4 pages).*
Clearco Products (Viscosity Conversion Chart. Clearco Products. 2016, 1 page).*
Sigma-Aldrich (Product Specification Sheet for Dimethyloctadecyl[3-(trimethoxysilyl) propyl]ammonium chloride, Sigma-Aldrich, 2011, 1 page).*
MicroStarLab (JIS Z 2801:2010 Antimicrobial Products—Test for Antimicrobial Activity and Efficacy. MicroStarLab. 2014, 4 pages).*
Fuller (Fulatex PD0124 Technical Data Sheet. Universal Selector. 2016, 2 pages).*
Dow (Rovace 661 Vinyl-Acrylic Emulsion Technical Data Sheet. Dow. 2016, 4 pages).*
Garrison (The Graphic Standards Guide to Architectural Finishes: Painting. ARCOM The American Institute of Architects. 2002, p. 218).*
Mattiello (Protective and Decorative Coatings: vol. III: Manufacture and Uses: Colloids, Oleoresinous Vehicles and Paints, Water and Emulsion Paints, Lacquers, Printing Inks, Luminescent Paints and Stains. Chapter 10B: Exterior Trim and Paints. 1943, pp. 315-322).*
Popular Mechanics (Giant Home Improvement Guide: Paint. Popular Mechanics. Apr. 2003, pp. 138-141).*
Koleske (Paint and Coating Manual, 14th Edition of the Gardner-Sward Handbook: Chapter 59 Architectural Coatings. 1995, pp. 696-705).*

(Continued)

*Primary Examiner* — Brieann R Johnston
(74) *Attorney, Agent, or Firm* — Daniel S. Ward; James C. Scott; Vivien Y. Tsang

(57) ABSTRACT

A high quality paint formulation comprises water, latex polymer, pigment, and a quaternary ammonium compound. The high quality paint is capable of killing gram positive bacteria, gram negative bacteria at a rate of greater than 3 logs within 2 hours of application of bacteria to a painted surface. The high quality paint is also capable of inactivating viruses.

43 Claims, No Drawings

(56) References Cited

OTHER PUBLICATIONS

Resene (Volume solids, PVC and hiding power. NZIA-Resene CPD. Aug. 2005, 14 pages).*
Accuratus (AOAC Method 961.02 Germidical Spray Method. Accuratus Lab Services. 2018, 1 page).*

* cited by examiner

HIGH QUALITY ANTIMICROBIAL PAINT COMPOSITION

This application is a continuation of patent application Ser. No. 13/552,966, filed Jul. 19, 2012, the entirety of which is hereby incorporated by reference, which in turns claims the benefit of U.S. Provisional Patent Application No. 61/541,168, filed Sep. 30, 2011, the entirety of which is hereby incorporated by reference.

This invention was made with Government support under Contract Number W911NF09C0025 awarded by the U.S. Army Research Office. The Government has certain rights in this invention.

FIELD OF THE INVENTION

This invention relates to a high quality latex paint which contains an antimicrobial agent, in particular a quaternary ammonium compound.

BACKGROUND

Paints typically contain four essential ingredients: carrier liquid, binder, pigment, and additives. Each of such ingredients may comprise a single component or several different items mixed into the paint.

The carrier liquid is a fluid component of the paint which serves to carry all of the other paint components. The carrier liquid is part of the wet paint and usually evaporates as the paint forms a film and dries on a surface. In latex paints, the carrier liquid is usually water. In oil-based paints, the carrier liquid is usually an organic solvent. The amount and type of liquid is usually determined by features of the other paint components.

The binder component of a paint is what causes the paint to form a film on and adhere to a surface. In a latex paint, the binder comprises a latex resin, usually selected from acrylics, vinyl acrylics, or styrene acrylics. In a latex paint, the latex resin particles usually are in a dispersion with water as the carrier liquid.

Pigments provide the paint with both decorative and protective features. Pigments are solid particles used to provide the paint with various qualities, including but not limited to color, opacity, and durability. The paint may also contain other solid particles such as polyurethane beads or other solids. Pigments and other solids add bulk to the paint and their levels are related to the gloss or flatness of the paint.

A multitude of additives may be included in paints. The additives are typically used at relatively low levels in the paint formulation, but contribute to various properties of paints, including rheology, stability, paint performance, and application quality.

Biocides, or specifically, antibacterial agents, are additives which have bacteriostatic and bactericidal properties. Biocides work to kill bacteria by one or more of several different mechanisms, including but not limited to interfering with cell wall synthesis, damaging the cell membranes, inhibiting protein synthesis, and interfering with nucleic acid synthesis. Some biocides may also have anti-viral effects, serving to inactivate viruses, such as cold and flu viruses.

A variety of biocidal agents are well known and are used for various purposes. Such biocides include inorganic biocidal agents, for example, those containing metal ions, such as silver, zinc, and copper. Other inorganic biocides include phosphates, metal ion, metal or other biocide containing zeolites or hydroxyapatites. There are also organic biocides including organic acids, phenols, alcohols, and quaternary ammonium compounds.

Quaternary ammonium compounds act as biocides by damaging cell membranes and killing bacteria. This mechanism is likely due to the positive charge on the quaternary ammonium compounds which interact with the negative charge sites of the bacteria.

Quaternary ammonium compounds are not typically added to latex paints, due to a negative effect on the quality of the paint. The prior art has recognized that when added to latex paints, quaternary ammonium compounds cause an undesirable increase in viscosity and cause the polymer and pigments to precipitate. Without being limited to any particular theory, it is believed that the cationic nature of the quaternary ammonium compounds is not compatible with the generally anionic nature of latex paint formulations which results in the precipitation of the components from the dispersion. The precipitation causes the paint to have an undesirable appearance as the precipitate particles cause the dry paint film to have a grainy appearance or texture.

DETAILED DESCRIPTION OF THE INVENTION

The present invention comprises, in one embodiment, a paint composition comprising water, latex binder resin, pigment, and additives, wherein such additives include, but are not limited to, a quaternary ammonium compound. In one useful embodiment, the latex binder resin and the quaternary ammonium compound have a compatibility score of less than 0.7 g, for example, less than 0.5 g, and further for example, less than 0.35 g, as measured by the Polymer/Quaternary Ammonium Compound Compatibility Test (hereinafter "Compatibility Test") described herein. In another embodiment, the invention comprises a high quality paint composition having broad spectrum biocidal capabilities. In one useful embodiment, the dried paint film is capable of reducing gram positive bacteria, gram negative bacteria, and viruses by greater than 3 logs within 2 hours of application of the bacteria or viruses to the coated surface. Bacterial and viral reduction is measured in a test based on the Japanese Industrial Standard (JIS) Z 2801 as described herein and compared to a control paint that does not contain a quaternary ammonium compound.

In a particularly useful embodiment, the paint composition of the present invention has one or more of the following characteristics: pigment volume concentration (PVC) of less than 60, about 25% to about 65% by weight solids, at least 17% by weight binder up to about 55% by weight binder polymer solids, and at least 10% by weight of a hiding pigment, for example, titanium dioxide. In one useful embodiment of the invention, the pigments used in the paint composition have a minimum fineness of grind by Hegman gauge of at least 4, for example, at least 5. Further, the paint composition may have one or more of the following qualities: good application and appearance, good stability, and good durability. Good application and appearance refers to one or more of the following properties: flow and leveling, color uniformity, durability of tinted coating to shear, contrast ratio, tint strength, and applied hide. Good durability refers to one or more of the following properties: abrasive scrub resistance as measured by ASTM Test Method D 2486-74A (>400 scrubs), block resistance measured by ASTM-D 4946-89, (>6 after 1 day and 7 days), and adhesion measured by ASTM-D3359 Test Method A (greater than 3 A). In another useful embodiment, the paint composition, when applied to a surface and dried, has a Gloss at 60° of 5-85 units, for example, over 5 up to 85 units.

The term "quaternary ammonium compounds" as used herein refers to quaternary ammonium salt antibacterial agents having the structural formula:

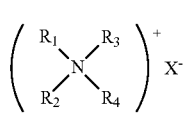

Formula I wherein $R_1$ and $R_2$ are linear or branched chain alkyl groups or mixtures of groups having 1-7 carbons, $R_3$ is a linear or branched chain alkyl group or mixtures of groups containing 6-20 carbons, and $R_4$ is selected from linear or branched chain alkyl groups or mixture of groups having 6-20 carbons, benzyl or C1-C18 alkyl benzyl groups, or

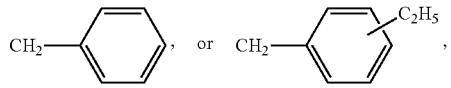

where $R_3$ and $R_4$ may be the same or different from each other, and X represents a halide, in particular chloride, bromide or iodide, carbonate, methosulfate, or saccharinate. In a particularly useful embodiment the quaternary ammonium compound does not contain or is substantially free of silicon species. Useful examples of quaternary ammonium compounds include, but are not limited to n-alkyl (C8-C18) dimethyl benzyl ammonium chlorides, benzalkonium chloride (where the alkyl side chain is C8, C10, C12, C14, C16 or C18 or mixtures thereof), n-alkyl (C8-C18) dimethyl ethylbenzyl ammonium chlorides, dialkyl dimethyl ammonium chlorides (where the alkyl side chain is C6-C12), n-alkyl dimethyl benzyl ammonium chloride, and didecyl dimethyl ammonium chloride, octyl decyl dimethyl ammonium chloride, dioctyl dimethyl ammonium chloride, didecyl dimethyl ammonium chloride, and mixtures of same. A variety of useful quaternary ammonium compounds are commercially available including, but not limited to Barquat®MB-50, Barquat®MB-80, and Bardac® 2250 quaternary ammonium compounds available from Lonza, Inc., BTC®1010, BTC®2125, and BTC®818-80% available from Stepan Company. Other useful quaternary ammonium compounds may include compounds having the following structures:

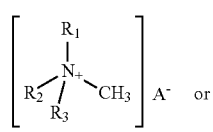

Formula II

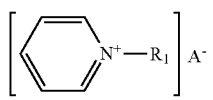

Formula III where $R_1$ is $C_8$-$C_{18}$-alkyl or -alkenyl, for example, -alkyl, where $R_2$ is $C_8$-$C_{18}$-alkyl or -alkenyl, for example, -alkyl, aryl or $C_7$-$C_{18}$-aralkyl, in which the aromatic rings can additionally be substituted, for example by chlorine and/or bromine, where $R_3$ is $C_1$-$C_4$-alkyl, for example, methyl, and can be identical or different, where $R_4$ is H or methyl, and where A is an anion of an organic or inorganic acid. Possible anions A are, for example, chloride, bromide, acetate, propionate, benzoate or 1 equivalent of sulfate. The radicals $R_1$ and $R_2$ in Formula II can be identical or different. For example, in one useful embodiment, compounds of Formula II in which $R_1$ and $R_2$ are $C_{10}$-$C_{12}$-alkyl or both radicals $R_1$ and $R_2$ are $C_{10}$-$C_{12}$-alkyl may be used. Compounds of the Formulas II and III are, for example, octyl-trimethylammonium bromide, decyl-trimethyl-ammonium chloride, didecyl-dimethylammonium chloride, dedecyl-methylhydroxyethylammonium propionate, lauryl-trimethylammonium chloride, lauryl-pyridinium chloride, hexadecyl-trimethyl-ammonium chloride, stearyl-trimethylammonium chloride and stearyl-dimethylbenzylammonium chloride. Paint compositions in accordance with the present invention may contain a single quaternary ammonium compound, as described above, or mixtures of two or more quaternary ammonium compounds.

A paint composition made in accordance with the present invention may comprise about 0.25% by weight up to about 3% by weight, for example, about 0.5% to about 1.5% of at least one quaternary ammonium compound.

Paint compositions in accordance with the present invention generally comprise at least about 17%, for example, at least about 17.5% by weight, to about 55% by weight of binder polymer solids. Binders useful in latex paint compositions are known in the art and include polymeric binders, such as acrylics, vinyl acrylics, or styrene acrylics binders. In one embodiment of the present invention, the paint composition is formulated to have a binder which is particularly compatible with the quaternary ammonium compound to avoid precipitation. The compatibility of the binder with the quaternary ammonium compound is determined by observing and measuring the degree of precipitation of binder and pigment when the quaternary ammonium compound is added to the paint composition as described in detail below:

Polymer/Quaternary Ammonium Compound Compatibility Test

Polymer preparation: Selected commercially available and proprietary polymers were diluted to 23.5% weight solids in water.

Quaternary Ammonium compound preparation: Selected commercially available quaternary ammonium compounds were diluted to 50% of their original concentration in water to enhance accurate delivery. (BTC®2125M-80, BTC®I210, BTC@I010 and BTC®818 quaternary ammonium compounds from Stepan and Barquat@MB-50 and Bardac® 2250 quaternary ammonium compounds from Lonza.

20.0 g of diluted polymer was mixed by hand with sufficient diluted quaternary ammonium compound to yield a concentration of 0.28% active quaternary ammonium compound in the 20.0 g polymer. The mixture was stirred slowly for 5 minutes and allowed to sit at room temperature, covered, for 1 hour. Any liquid was poured off from the vessel. The remaining solids were allowed to dry overnight at 70-77° F. then weighed. A control for each polymer with no quaternary ammonium compound was prepared and the solids weight of the control was subtracted from the weight of the corresponding polymer/quaternary ammonium compound samples in order to account for any losses during handling. The weight of solids observed minus the weight of the control solids results in the compatibility score. The binder polymers tested are listed in Table 1. The quaternary ammonium compounds tested are listed in Table 2. The results of compatibility testing for selected polymer/quaternary ammonium compound pairs is listed in Table 3. The term "compatibility score" for a polymer as used herein refers to the average compatibility score for that polymer with the six quaternary ammonium compounds tested and listed in Table 3.

TABLE 1

| Polymer | Monomer Chemistry | Stabilization Chemistry | Zeta Potential (mV) | pH | Diameter* (nm) |
| --- | --- | --- | --- | --- | --- |
| UCAR™ 6045[1] | Vinyl acrylic | Nonionic | −7.75 | 4.79 | 220 |
| UCAR™ 461[2] | Styrene acrylic | Nonionic | −7.08 | 9.03 | 98.5 |
| ROVACE™ 661[3] | Vinyl acetate/butyl acrylate | Nonionic | −2.6 | 4.33 | 328 |
| JONCRYL® 537[4] | Acrylic | Anionic/Nonionic | −13.14 | 9.08 | 64 |
| JONCRYL® 1530[5] | Acrylic | Anionic/Nonionic | −24.77 | 8.14 | 135 |
| VINNAPAS® EF-811[6] | Vinyl acrylic | Anionic | −20.66 | 4.15 | 214 |
| ACRONAL OPTIVE® 130[7] | Acrylic | Anionic | −14.82 | 7.98 | 162 |
| Proprietary polymer A[8] | Vinyl acrylic | Anionic/Nonionic | −10.1 | 4.76 | 277 |
| Proprietary polymer B[8] | Acrylic | Anionic/Nonionic | −5.49 | 8.79 | 89.6 |

TABLE 1-continued

| Polymer | Monomer Chemistry | Stabilization Chemistry | Zeta Potential (mV) | pH | Diameter* (nm) |
| --- | --- | --- | --- | --- | --- |
| Proprietary polymer C[8] | Latex acrylic alkyd | Anionic | −20.69 | 7.89 | 111.3 |
| Proprietary polymer D[8] | Styrene-acrylic | Anionic | −13.71 | 8.55 | 911 |
| Proprietary polymer E[8] | Styrene-acrylic | Anionic | −21.75 | 8.36 | 89.9 |
| Proprietary polymer F[8] | Styrene-acrylic | Anionic | −7.75 | 4.79 | 220 |
| Proprietary polymer G[8] | Styrene-acrylic | Anionic | −17.26 | 7.98 | 87.4 |
| Proprietary polymer H[8] | Acrylic | Anionic/nonionic | −22 | 7.96 | 153 |
| Proprietary polymer I[8] | Vinyl acrylic | Nonionic | −3.22 | 5.15 | 311 |
| Combination of UCAR™6045/Prop B (75/25) | | Nonionic | −4.3 | 5.15 | |
| Combination of Prop D and Prop E (50/50) | | Anionic | −18.64 | 8.46 | |

*Intensity average diameter measured by a Malvern Zetasizer Nano-S Dynamic Light Scattering Instrument.
[1]Available from Arkeina, Inc.
[2]Available from Arkema, Inc.
[3]Available from Dow.
[4]Available from BASF.
[5]Available from BASF.
[6]Available from Wacker Chemie.
[7]Available from BASF.
[8]Proprietary polymers made by the assignee of the present application.

TABLE 2

| Quaternary Ammonium Compound Trade Name | Chemical Structure (% Active) |
| --- | --- |
| BTC ®2125 M | n-Alkyl (60% C14, 30% C16, 5% C12, 5% C18) Dimethyl Benzyl Ammonium Chloride (40%) n-Alkyl (68% C12, 32% C14) Dimethyl Ethylbenzyl Ammonium Chloride (40%) |
| BTC ® 1210 | Didecyl dimethyl ammonium chloride (48.0%) Alkyl (50% C14, 40% C12, 10% C16) dimethyl benzyl ammonium chloride (32.0%) |
| BARQUAT ® MB-50 | Alkyl (C14 50%, C16 10%, C12 40%) Dimethyl Benzyl Ammonium Chloride (50%) |
| BTC ® 1010 | Didecyl dimethyl ammonium chloride (80%) |
| BARDAC ® 2250 | Didecyl dimethyl ammonium chloride (50%) |
| BTC ® 818 | Octyl decyl dimethyl ammonium chloride (80%) |

TABLE 3

| Polymer | BTC2125M Score (g) | BTC 1210 Score (g) | BARQUAT MB-50 Score (g) | BTC 1010 Score (g) | BARDAC 2250 Score (g) | BTC 818 Score (g) | Average | Standard deviation |
|---|---|---|---|---|---|---|---|---|
| Prop1 | 0.06 | 0.02 | 0.07 | 0.04 | 0.01 | 0.01 | 0.04 | 0.03 |
| UCAR ™ 6045/PropB (75/25) | 0 | 0.05 | 0.04 | 0.1 | 0 | 0.07 | 0.04 | 0.04 |
| PropA | 0.06 | 0.04 | 0.01 | 0 | 0.07 | 0.1 | 0.05 | 0.04 |
| PropB | 0 | 0.04 | 0.05 | 0.11 | 0.04 | 0.08 | 0.05 | 0.04 |
| PropC | 0.12 | 0.05 | 0.03 | 0.04 | 0.08 | 0.03 | 0.06 | 0.04 |
| UCAR ™ 6045 | 0.15 | 0.11 | 0.08 | 0.05 | 0.11 | 0.09 | 0.10 | 0.03 |
| Rovace ™ 661 | 0.14 | 0.12 | 0.19 | 0.15 | 0.09 | 0.05 | 0.12 | 0.05 |
| PropF | 0.04 | 0.06 | 0 | 0.47 | 0.14 | 0.08 | 0.13 | 0.17 |
| Joncryl ® 537 | 0.02 | 0.23 | 0.08 | 0.27 | 0.04 | 0.19 | 0.14 | 0.11 |
| UCAR ™ 461 | 0.09 | 0.16 | 0.07 | 0.16 | 0.19 | 0.21 | 0.15 | 0.06 |
| PropD | 0.11 | 0.38 | 0.03 | 0.4 | 0.4 | 0.37 | 0.28 | 0.17 |
| PropE | 0 | 0.27 | 0.08 | 0.51 | 0.64 | 0.31 | 0.30 | 0.24 |
| D/E (50/50) | 0.15 | 0.52 | 0.13 | 0.03 | 0.53 | 0.6 | 0.33 | 0.25 |
| PropG | 0 | 0.38 | 0.34 | 0.34 | 0.5 | 0.51 | 0.35 | 0.19 |
| Joncryl ® 1530 | 0.25 | 0.5 | 0.55 | 0.33 | 0.54 | 0.48 | 0.44 | 0.12 |
| Vinnapas ® EF811 | 0.97 | 0.23 | 1.52 | 0.42 | 0.36 | 0.72 | 0.70 | 0.48 |
| PropH | 0.78 | 0.86 | 0.89 | 4.82 | 0.8 | 0.8 | 0.83 | 0.04 |
| Acronal Optive ® 130 | 0.54 | 0.73 | 1.58 | 0.76 | 1.19 | 0.98 | 0.96 | 0.38 |

The compatibility score for each polymer is the average score for the above test for all of the six quaternary ammonium compounds tested. In one embodiment of the invention, the polymer has a compatibility score of 0.7 or less. In one particularly useful embodiment, the polymer used in paint compositions in accordance with the present invention has a compatibility score of 0.5 or less. In a particularly preferred embodiment, the polymer used in paint compositions in accordance with the present invention has a compatibility score of 0.35 or less. It should be noted that the average is used as the compatibility score rather than the score for individual polymer/quaternary ammonium compound pairs. It has been determined that for polymers that have an average compatibility score of 0.7 or higher, even if a specific polymer/quaternary ammonium compound pair had an individual score of less than 0.7, that pair was not capable of making a stable composition as defined herein. It has also been determined that for polymers having an average score of 0.5 or less, that a pair having an individual score of above 0.5 were able to make a stable composition.

The prior art has typically taught away from using quaternary ammonium compounds in latex paints, because the combination results in precipitation, i.e. a less stable composition. In one useful embodiment, the paint composition of the present invention is stable at room temperature for at least one week, for example, at least two weeks, and is also stable at 120° F. for at least one week, for example, at least two weeks. As used herein, a "stable" composition has a change in viscosity of less than 15 Krebs Units ("KU") measured by a Stormer Electronic Viscometer Model KU1+ (sample measured in a pint sized paint can, filled ¾ full and adjusted to 77° F.±1° F.) after 1 week at 120° F. after the addition of a quaternary ammonium compound to the composition. In another useful embodiment of the invention, the paint composition has a viscosity under 120 KU, for example from 85-120 KU, further for example, about 90-110 KU as measured by a Stormer Electronic Viscometer Model KU1+.

The results of the stability test are unexpected and surprising considering the zeta potential of the tested polymers. In general the magnitude of the zeta potential is an indicator of the stability of the polymer. Polymer particles with a large (either negative or positive) zeta potential tend to repel each other and are less likely to come together and flocculate or precipitate out of the dispersion. In general, particles with zeta potentials more positive than +30 mV or more negative than −30 mV are considered more stable. Indeed, particles with zeta potentials of −5 mV to +5 mV generally see rapid flocculation with particles having zeta potentials of ±5 mV to ±30 mV being only slightly more stable. In one embodiment of the present invention, useful polymers include those with zeta potentials between 0 mV and ±30 mV, for example, polymers with zeta potentials between 0 mV and ±25 mV.

The paint composition of the present invention further comprises at least about 10% by weight pigments. Such pigments may comprise inorganic pigments, such as titanium dioxide. The high quality paint composition comprises, for example, at least about 11% by weight, further for example, at least about 12% by weight, further for example, at least about 13% by weight, further for example, at least about 14% by weight, further for example at least about 15% by weight, further for example, at least about 16%, further for example at least about 17%, further for example, at least about 18%, further for example at least about 19%, and even further for example at least about 20% up to about 30% by weight titanium dioxide. In another useful embodiment, the high quality paint composition comprises more than 10% titanium dioxide. Other colored pigments or dyes may also be added to the paint, alone or in combination, to produce a wide range of colored paint. Suitable additional pigments may include calcium carbonate, talc, clay, silicates, aluminum silicates, calcium metasilicates, aluminum potassium silicates, magnesium silicates, barium sulfates, nepheline syenite, feldspar, zinc oxides or sulfides, or others known to those skilled in the art. Such additional colored pigments may be included in amounts up to about 30% by weight, for example, about 10% to about 20%. In some cases, "pigments" may also refer to functional fillers which are non-water soluble solids. Such functional fillers may include solids which provide additional functional characteristics to the paint, for example, intumescent ingredients, such as ammonium polyphosphates, melamines, pentaerythritol and similar compounds. In one useful embodiment, the coating composition of the present invention is substantially free or totally free of intumscent ingredients such as ammonium polyphosphates, melamines, and pentaerythritol and similar compounds.

The pigment volume concentration, or PVC, of a coating is the ratio of the volume of pigments (including functional fillers) to the volume of total non-volatile material (i.e. pigment and binder) present in the coating. The coating of the present invention preferably has a PVC of about 5 to about 60. In addition, the coating composition of the present invention has a maximum solids content of less than 65% by weight, for example, about 25% by weight to about 60% by weight, further for example about 30% by weight to about 58% by weight.

The composition may also include various other additives, including but not limited to thickeners, such as urethane thickeners, and acrylic thickeners in amounts up to about 10% by weight, for example about 1% to about 2%. Synthetic organic materials might also be incorporated; these include plastic beads, hollow spheres or other similar materials. Other optional components include glycols such as ethylene and/or propylene glycol in amounts up to about 7% and other solvents such as diethylene glycol dibenzoate and dipropylene glycol dibenzoate in amounts up to about 3%. The coating composition may also contain pigment dispersing agents which can be solvents or surfactants; wet paint preservatives; dry film preservatives; foam control agents such as oils, fatty acids and silicones; slip and mar additives; adhesion promoters, and/or other known paint additives.

The paint composition of the present invention may also comprise other biocides including but not limited to metal ion containing compounds, polymeric biocides, heterocyclic compounds, phenols, organometallics, aldehydes, proteins, peroxygens, alcohols, enzymes, polypeptides, and halogen releasing compounds.

Paints made in accordance with the present invention are generally formulated to have a pH between 7 and 10.

It has been observed that by premixing the quaternary ammonium compounds with a mixture of ester alcohols and oleic acid monoester propylene glycols that higher concentrations of quaternary ammonium salts can be achieved. This method comprises mixing together quaternary ammonium compound, with an ester alcohol, such as Texanol™ solvent, and oleic acid monoester propylene glycol, such as Loxanol® EFC, and then adding the mixture to the paint composition. In one embodiment, the ester alcohol and oleic acid monoester propylene glycol are functional components of the paint composition. In one useful embodiment the ester alcohol and oleic acid monoester propylene glycol are added to the paint composition only by this method. In another embodiment, portions of the normally used amounts of the ester alcohol and oleic acid monoester propylene glycol are used to prepare the premix. For example, in one embodiment, about half of the normally used amounts of the ester alcohol and oleic acid monoester propylene glycol may be mixed with the quaternary ammonium compound for addition to the paint composition.

In another embodiment, the quaternary ammonium compound included in the paint composition may be encapsulated within a solid shell ("microcapsule") material. Microencapsulation of the quaternary ammonium compound serves to protect the paint from flocculation by minimizing or eliminating direct interactions between the quaternary ammonium compounds and the latex binder and other paint ingredients. In one embodiment, the microcapsule completely isolates the quaternary ammonium compound from interaction with the other paint components. The microcapsule may have a structure which allows it to isolate the quaternary ammonium compound from the rest of the paint components, but opens or bursts upon drying of the paint film to allow the quaternary ammonium compound to contact and kill or inactivate microorganisms or viruses which come into contact with the dried paint film surface. For example, the capsule could be designed to open as the pH of the system changes as the paint dries. In another embodiment, the evaporation of water from the system could cause the capsule to desiccate and burst. Means for encapsulating active materials (also referred to as delivery systems) are known to those of ordinary skill in the art. Any such methods which are known or are later developed may be used in this invention.

It should be noted that in order to make a latex paint formulation, an appropriate dispersant/surfactant system is needed in order to disperse the pigments in the paint formulation. The process for selecting dispersants/surfactants for paint formulations is well known to those of ordinary skill in the paint formulation art. After selecting a compatible polymer and quaternary ammonium compound as described herein, one of ordinary skill in the art would be able to select a dispersant/surfactant combination in order to make a desired paint composition.

In one useful embodiment, the dried paint film is capable of reducing gram positive bacteria, gram negative bacteria, and viruses by greater than 3 logs within 2 hours of application. The bacterial and viral reduction is measured in a test based on the JIS Z 2801 modified for paints as described herein and compared to a control paint that does not contain a quaternary ammonium compound.

EXAMPLES

Exemplary stable, high quality paint formulations were made by mixing the following components using techniques known to those of ordinary skill in the art:

Comparative Example

| COMPONENT | Weight % |
| --- | --- |
| UCAR™ 6045 | 30.62 |
| Proprietary Polymer B (55% solids) | 8.19 |
| Defoamer[1] | 0.25 |

-continued

| COMPONENT | Weight % |
|---|---|
| WATER | 19.73 |
| Hydroxyethyl cellulose thickener[2] | 0.02 |
| Dispersant[3] | 0.49 |
| Titanium Dioxide (dry) | 23.29 |
| Pigment[4] | 9.05 |
| Pigment[5] | 3.45 |
| Coalescent[6] | 0.26 |
| Rheology modifier[7] | 2.85 |
| Rheology modifier[8] | 1.29 |
| Nonionic surfactant[9] | 0.43 |
| Aqueous ammonia | 0.08 |
| Total | 100 |

[1]BYK ® 024 from Byk Chemie
[2]CELLOSIZE™ QP-4400H from Dow
[3]TAMOL™ 1254 from Dow.
[4]MINEX™ 4 from Unimin Specialty Minerals
[5]MINEX™ 2 from Unimin Specialty Minerals
[6]LOXANOL™ EFC 100 from Cognis
[7]ACRYSOL™ RM-8W from Dow
[8]ACRYSOL™ RM-2020 NPR from Dow
[9]TRITON™ X-102 from Dow Example 1 was made by adding 0.65 g of Barquat MB-80 Quaternary Ammonium Compound to a paint prepared in accordance with the Comparative Example then stirring with an air mixer at room temperature for 10 minutes.

Paint compositions as described herein were tested for antimicrobial activity. Paint coupons for the bacterial testing were made using the following procedure: A 7 mil wet film caster was used to draw down HARMONY® interior acrylic latex (flat, extra white) paint on a black Leneta scrub chart P121-10N. The base coat was air dried overnight and a 7 mil film caster was then used to draw down the paint of Example 1 over it. After air drying overnight, a second 7 mil coating of Example 1 was applied and allowed to air dry overnight. A control with a base coat of Harmony® interior acrylic latex paint and two coats of the Comparative Example paint was made using the same process. An additional control sample consisting of unpainted Leneta chart was tested in the same manner as the paint samples.

To test the paint's ability to kill bacteria, Japanese Industrial Standard JIS Z 2801 was used with the following adaptations: The E. coli ATCC 11229 was used instead of ATCC8739 and 0.3 ml organic soil load (25 mL Fetal Bovine Serum+5 mL Triton X-100) was added to the culture. Three 1 in×1 in pieces of Parafilm laboratory film were placed in a sterile glass Petri dish and a 20 cm×20 cm sample from the center of the paint drawdown was placed on each of the prepared coupons. Twenty-five μl of inoculum were placed on the paint surface. After inoculation, the samples were covered with a glass coverslip and incubated for 2 hours at saturation humidity. The comparative example paint was processed in the same way as the paint of Example 1. The bacteria was recovered by placing the paint square, parafilm and coverslip in a sterile 50 ml conical tube filled with 5 ml of phosphate buffered saline (PBS) and vortexed for 15-30 seconds to release the remaining bacteria back into solution. A total viable count (TVC) was performed on the eluent solution. Colony Forming Units/milliliter (CFU/ml) of bacteria recovered from each sample was calculated, and results were reported as the log reduction in CFU/ml of the antimicrobial paint compared to the untreated paint. A measurement of the CFU/ml of the inoculum was made by transferring 25 μl bacterial culture directly into a sterile 50 ml tube containing 5 ml of PBS, and completing the test method. The CFU/ml of the Staph innoculum was determined to be $9.7 \times 10^6$ and the CFU/ml of the E. Coli innoculum was determined to be $1.0 \times 10^6$. The effectiveness of the test conditions was judged to be adequate because the CFU/ml of the innoculum was between $2.5 \times 10^5$ and $1 \times 10^7$ CFU/ml and the CFU/ml of the unpainted Leneta chart and parafilm control and the comparative example were between 5 and 6.7 $Log_{10}$ CFU/ml.

The results of the antimicrobial testing for these paints are summarized in Table 4.

TABLE 4

| Sample | $Log_{10}$ CFU/ml, S. aureus 2 hrs | $Log_{10}$ CFU/ml, E. coli 2 hrs |
|---|---|---|
| Unpainted Control | 5.6 | 5.9 |
| Comparative example: | 5.5 | 5 3 |
| Example 1: | 1.2 | 1.3 |
| Log reduction | 4.4 | 4.6 |

Separate paint coupons for viral testing were made using the same procedure as described above for the bacterial testing except that no unpainted films were used. To test the paint's ability to inactivate viruses, the following procedure was used. A Stock Influenza A virus (ATCC VR-544 Strain Hong Kong) in Minimum Essential Medium, containing 1% fetal bovine serum was used in this test. The stock virus was stored at ≤−70° C. On the day of testing, the stock virus was titred by 10-fold serial dilutions and assayed for infectivity to determine the starting titer of the virus. The starting titer for the test was $1 \times 10^{7.75}$ $TCID_{50\%}/0.10$ ml.

Replicate 1 in×1 in coupons coated with the paints of the Comparative Example and Example 1 were placed in sterile Petri dishes. The coupons were irradiated with UV light for about 15 minutes on each side. The samples were inoculated with a 100 μl aliquot of the test virus. The inoculum was covered with carrier film (20 mm×20 mm prepared from a sterile stomacher bag) and the carrier film was pressed down so that the test virus spread over the film but did not spill over the edge of the film. The exposure time began when each sample was inoculated. The samples were transferred to a controlled chamber set at 20° C. in a relative humidity of 40% for the duration of the exposure times. The coupons were kept in contact with the virus for 1 or 2 hours at 20° C. and 40% relative humidity.

Following each exposure time, a 1.00 ml aliquot of test medium (Minimum Essential Medium supplemented with 1% v/v heat inactivated fetal bovine serum, 10 micrograms/ml gentamycin, 10 units/ml penicillin, and 2.5 micrograms/ml amphtericin B) was individually pipetted onto each test and control paint coupons as well as to the underside of the film used to cover each sample. The surface of each paint coupon was scraped with a sterile plastic cell scraper. The test medium was collected, mixed using a vortex type mixer and serial 10-fold dilutions were prepared. The serial dilutions were assayed for infectivity on Rhesus monkey kidney cells. The geometric mean of two $TCID_{50\%}$. (Tissue Culture Infective Dose)/0.1 ml replicates for each of the Comparative example and Example 1 was determined and the log reductions at each contact time were calculated by subtracting the result of Example 1 from the Comparative Example.

The results of the viral testing for paints made in accordance with the present invention are summarized in Table 5

TABLE 5

| Sample | Mean TCID$_{50\%}$/0.1 ml (Tissue Culture Infective Dose) at 1 hour | Mean TCID$_{50\%}$/0.1 ml (Tissue Culture Infective Dose) at 2 hours |
|---|---|---|
| Comparative control: | 7.63 Log$_{10}$ | 7.38 Log$_{10}$ |
| Inventive example: | ≤1.5 Log$_{10}$ | ≤1.5 Log$_{10}$ |
| Log reduction | ≥6.13 | ≥5.88 |

The invention claimed is:

1. A paint composition comprising:
   (a) a binder polymer having a compatibility score of 0.5 or lower;
   (b) a quaternary ammonium compound;
   (c) at least about 20% by weight titanium dioxide pigment; and
   (d) water;
   wherein the paint composition has a total solids content of less than 60% by weight and a viscosity of under 120 KU,
   wherein the paint composition has a pigment volume concentration (PVC) of about 5 to about 60;
   wherein the quaternary ammonium compound is present in a suitable amount to provide one or more of (1) gram negative bacterial reduction by greater than 3 logs within 2 hours of application of the gram negative bacteria to a dried surface of the paint composition; (2) gram positive bacterial reduction by greater than 3 logs within 2 hours of application of the gram positive bacteria to a dried surface of the paint composition; or (3) viral reduction by greater than 3 logs within 2 hours of application of the virus to a dried surface of the paint composition.

2. The paint composition of claim 1, wherein the composition further comprises one or more of calcium carbonate, talc, clay, silicates, aluminum silicates, calcium metasilicates, aluminum potassium silicates, magnesium silicates, barium sulfates, nepheline syenite, feldspar, zinc oxides, sulfides, or mixtures thereof.

3. The paint composition of claim 1, further comprising at least one pigment other than titanium dioxide in an amount up to about 30% by weight.

4. The paint composition of claim 1, wherein the paint composition is substantially free of an intumescent ingredient.

5. The paint composition of claim 1, wherein the paint composition has about 30% to about 60% by weight solids.

6. The paint composition of claim 1, wherein the paint composition exhibits a change in viscosity of less than 15 KU after 1 week at 120° F.

7. The paint composition of claim 1, wherein the paint composition has a viscosity of 85 KU to under 120 KU.

8. The paint composition of claim 1, wherein the quaternary ammonium compound is present at about 0.25% to about 3% by weight.

9. The paint composition of claim 1, wherein the quaternary ammonium compound has the structural formula:

$$\left( \begin{array}{c} R_1 \quad R_3 \\ N \\ R_2 \quad R_4 \end{array} \right)^+ X^-$$

wherein $R_1$ and $R_2$ are linear or branched chain alkyl groups or mixtures of groups having 1-7 carbons, $R_3$ is a linear or branched chain alkyl group or mixtures of groups containing 6-20 carbons, and $R_4$ is selected from linear or branched chain alkyl groups or mixture of groups having 6-20 carbons, benzyl or $C_1$-$C_{18}$ alkyl benzyl groups, or $$CH_2-\bigcirc \quad\quad CH_2-\bigcirc-C_2H_5$$

where $R_3$ and $R_4$ may be the same or different from each other, and X represents a halide, the halide is selected from chloride, bromide or iodide, carbonate, methosulfate, or saccharinate.

10. The paint composition of claim 1, wherein the quaternary ammonium compound has the structural formula:

$$\left[ \begin{array}{c} R_1 \\ | \\ R_2-N^+-CH_3 \\ | \\ R_3 \end{array} \right] A^- \quad \text{Formula II}$$

or $$\left[ \bigcirc N^+-R_1 \right] A^- \quad \text{Formula III}$$

where $R_1$ is $C_8$-$C_{18}$-alkyl or -alkenyl, where $R_2$ is $C_8$-$C_{18}$-alkyl or -alkenyl, in which the aromatic rings can additionally be substituted, and where $R_3$ is $C_1$-$C_4$-alkyl.

11. The paint composition of claim 1, wherein the quaternary ammonium compound is one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof.

12. The paint composition of claim 1, wherein the quaternary ammonium compound is substantially free of silicon.

13. The paint composition of claim 1, wherein the quaternary ammonium compound is in a microcapsule.

14. The paint composition of claim 1, wherein the binder polymer is present at about 7% to about 30% by weight.

15. The paint composition of claim 1, wherein the binder polymer is one or more of acrylics, vinyl acrylics, styrene acrylics or mixtures thereof.

16. The paint composition of claim 1, wherein the binder polymer has a zeta potential between 0 mV and ±30 mV.

17. The paint composition of claim 1, wherein the paint composition has a dried paint film gloss of up to 85 gloss units measured at 60°.

18. The paint composition of claim 1, wherein the paint composition has a dried paint film gloss over 5 gloss units measured at 60°.

19. The paint composition of claim 1, wherein the paint composition has a dried paint film gloss of 5 to 85 gloss units measured at 60°.

20. The paint composition of claim 1, wherein the pigment has a minimum fineness of grind by Hegman gauge of at least 4.

21. The paint composition of claim 1, wherein the pigment has a minimum fineness of grind by Hegman gauge of at least 5.

22. The paint composition of claim 1, wherein the paint composition has a pH between 7 and 10.

23. The paint composition of claim 1, the paint composition further comprising a pigment dispersing agent.

24. The paint composition of claim 23, wherein the pigment dispersing agent is a solvent or surfactant.

25. The paint composition of claim 23, wherein the pigment dispersing agent is present at lower than about 0.5% by weight.

26. The paint composition of claim 1, the paint composition further comprising one or more biocides selected from metal ion containing compounds, polymeric biocides, heterocyclic compounds, phenols, organometallics, aldehydes, proteins, peroxygens, alcohols, enzymes, polypeptides, or halogen releasing compounds.

27. A paint composition comprising:
(a) a binder polymer having a compatibility score of 0.5 or lower;
(b) a quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof;
(c) at least about 20% by weight titanium dioxide;
(d) a pigment other than titanium dioxide; and
(e) water;
wherein the paint composition has a total solids content of less than 60% by weight and a viscosity of under 120 KU,
wherein the paint composition has a pigment volume concentration (PVC) of about 5 to about 60;
wherein the quaternary ammonium compound is present in a suitable amount to provide one or more of (1) gram negative bacterial reduction by greater than 3 logs within 2 hours of application of the gram negative bacteria to a dried surface of the paint composition; (2) gram positive bacterial reduction by greater than 3 logs within 2 hours of application of the gram positive bacteria to a dried surface of the paint composition; or (3) viral reduction by greater than 3 logs within 2 hours of application of the virus to a dried surface of the paint composition.

28. The paint composition of claim 27, wherein the binder polymer has a zeta potential between 0 mV and ±30 mV.

29. The paint composition of claim 27, the paint composition further comprising one or more biocides selected from metal ion containing compounds, polymeric biocides, heterocyclic compounds, phenols, organometallics, aldehydes, proteins, peroxygens, alcohols, enzymes, polypeptides, or halogen releasing compounds.

30. The paint composition of claim 27, wherein the paint composition has a dried film gloss of 5 to 85 gloss units measured at 60°.

31. The paint composition of claim 27, wherein the paint composition has a pH between 7 and 10.

32. The paint composition of claim 27, the paint composition further comprising a pigment dispersing agent.

33. A paint composition comprising:
(a) about 7% to about 30% by weight of a binder polymer having a compatibility score of 0.7 or lower;
(b) about 0.25% to about 3% by weight quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$), n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof;
(c) at least about 20% by weight pigment; and
(d) water; wherein the paint composition has a total solids content of less than 60% by weight and a viscosity of under 120 KU and a pigment volume concentration (PVC) of about 5 to about 60,
wherein the quaternary ammonium compound is present in a suitable amount to provide one or more of (1) gram negative bacterial reduction by greater than 3 logs within 2 hours of application of the gram negative bacteria to a dried surface of the paint composition; (2) gram positive bacterial reduction by greater than 3 logs within 2 hours of application of the gram positive bacteria to a dried surface of the paint composition; or (3) viral reduction by greater than 3 logs within 2 hours of application of the virus to a dried surface of the paint composition.

34. The paint composition of claim 33, wherein the paint composition has a pH between 7 and 10.

35. The paint composition of claim 33, wherein the paint composition exhibits a change in viscosity of less than 15KU after 1 week at 120° F.

36. The paint composition of claim 33, wherein the pigment wherein the pigment is one or more of calcium carbonate, talc, clay, silicates, aluminum silicates, calcium metasilicates, aluminum potassium silicates, magnesium silicates, barium sulfates, nepheline syenite, feldspar, zinc oxides, sulfides, titanium dioxide or mixtures thereof.

37. The paint composition of claim 36, wherein the pigment is titanium dioxide in an amount of at least 20% by weight.

38. The paint composition of claim 37, further comprising at least one pigment other than titanium dioxide in an amount up to about 30% by weight.

39. A paint composition comprising:
(a) about 7% to about 30% by weight of a binder polymer having a compatibility score of 0.7 or lower;
(b) about 0.25% to about 3% by weight quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof;

(c) at least about 20% by weight pigment;

(d) a pigment dispersing agent; and (e) water; wherein the paint composition has a total solids content of less than 60% by weight and a viscosity of under 120 KU and a pigment volume concentration (PVC) of about 5 to about 60, wherein the quaternary ammonium compound is present in a suitable amount to provide one or more of (1) gram negative bacterial reduction by greater than 3 logs within 2 hours of application of the gram negative bacteria to a dried surface of the paint composition; (2) gram positive bacterial reduction by greater than 3 logs within 2 hours of application of the gram positive bacteria to a dried surface of the paint composition; or (3) viral reduction by greater than 3 logs within 2 hours of application of the virus to a dried surface of the paint composition.

40. The paint composition of claim 1, wherein the quaternary ammonium compound is present in a suitable amount to provide reduction of *E. Coli* ATCC 11229 by greater than 3 logs within 2 hours of application of the bacteria to a dried surface of the paint composition, the quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof.

41. The paint composition of claim 27, wherein the quaternary ammonium compound is present in a suitable amount to provide reduction of *E. Coli* ATCC 11229 by greater than 3 logs within 2 hours of application of the bacteria to a dried surface of the paint composition, the quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof.

42. The paint composition of claim 33, wherein the quaternary ammonium compound is present in a suitable amount to provide reduction of *E. Coli* ATCC 11229 by greater than 3 logs within 2 hours of application of the bacteria to a dried surface of the paint composition, the quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof.

43. The paint composition of claim 39, wherein the quaternary ammonium compound is present in a suitable amount to provide reduction of *E. Coli* ATCC 11229 by greater than 3 logs within 2 hours of application of the bacteria to a dried surface of the paint composition, the quaternary ammonium compound comprising one or more of n-alkyl dimethyl benzyl ammonium chlorides, the n-alkyl being a $C_8$-$C_{18}$ alkyl, benzalkonium chloride, the alkyl side chain being $C_8$, $C_{10}$, $C_{12}$, $C_{14}$, $C_{16}$ or $C_{18}$ or mixtures thereof, n-alkyl dimethyl ethylbenzyl ammonium chlorides, the n-alkyl being a $C_8$-$C_{18}$ alkyl, dialkyl dimethyl ammonium chlorides, the alkyl side chain being $C_6$-$C_{12}$, n-alkyl dimethyl benzyl ammonium chloride, dodecyl dimethyl ammonium chloride, octyl decyl dimethyl ammonium chloride, dioctyl dimethyl ammonium chloride, didecyl dimethyl ammonium chloride, or mixtures thereof.

* * * * *